(12) United States Patent
Ho

(10) Patent No.: US 11,612,511 B2
(45) Date of Patent: Mar. 28, 2023

(54) DEVICE AND METHOD FOR CLEANING EXCREMENTS

(71) Applicant: Chin-Hsuan Ho, Taipei (TW)

(72) Inventor: Chin-Hsuan Ho, Taipei (TW)

(*) Notice: Subject to any disclaimer, the term of this patent is extended or adjusted under 35 U.S.C. 154(b) by 1088 days.

(21) Appl. No.: 16/268,442

(22) Filed: Feb. 5, 2019

(65) Prior Publication Data

US 2020/0246172 A1 Aug. 6, 2020

(51) Int. Cl.
| | |
|---|---|
| *A61M 1/00* | (2006.01) |
| *A61M 3/06* | (2006.01) |
| *A61F 5/442* | (2006.01) |
| *A61F 5/44* | (2006.01) |
| *A61M 27/00* | (2006.01) |
| *B08B 3/04* | (2006.01) |
| *B08B 5/02* | (2006.01) |

(52) U.S. Cl.
CPC .......... *A61F 5/442* (2013.01); *A61F 5/4404* (2013.01); *A61M 3/06* (2013.01); *B08B 3/04* (2013.01); *B08B 5/02* (2013.01)

(58) Field of Classification Search
CPC .......... A61M 1/00; A61M 27/00; A61M 3/06; A61F 5/442; A61F 5/443; A61F 5/4404; A61F 5/4405; A61F 5/441; A61F 5/451; A61F 13/49007; B08B 3/04; B08B 5/02
See application file for complete search history.

(56) References Cited

U.S. PATENT DOCUMENTS

| | | | |
|---|---|---|---|
| 8,574,208 B1* | 11/2013 | Sippio | A61F 5/44 604/385.03 |
| 2020/0046384 A1* | 2/2020 | Ciccone | A61M 3/022 |

FOREIGN PATENT DOCUMENTS

JP 2008237420 A * 3/2007

* cited by examiner

*Primary Examiner* — Tatyana Zalukaeva
*Assistant Examiner* — Ilya Y Treyger
(74) *Attorney, Agent, or Firm* — Muncy, Geissler, Olds & Lowe, P.C.

(57) ABSTRACT

The present disclosure disclosed a device and a method for cleaning excrements. The device comprises a cleaning machine, an outer cover an inner body. The outer cover is wearable to a person and is coupled to the inner body. The inner body comprises at least one sensor and a cleaning assembly. The sensor is configured for sensing excrement and triggering the cleaning machine to collect the excrement through the tube. The cleaning assembly is connected to the cleaning machine and is configured for cleaning the person. The method comprises acts of cleaning excrement based on the modes and the excrement sensed result. Therefore, the present disclosure is able to assist people without autonomy to clean up excrements in a comfortable manner without others help.

9 Claims, 4 Drawing Sheets

DEVICE AND METHOD FOR CLEANING EXCREMENTS

FIELD OF THE INVENTION

Embodiments of the present disclosure relate to a cleaning method, and especially toward a method and a device that are able to assist people without autonomy to clean up excrements.

BACKGROUND

For those people without autonomy confined on bed which is unable or have difficulties to clean up his own urinary and fecal discharges, they will need other people's help (i.e., caregiver) to clean up it and maintain the cleanness and fresh. The most common way is providing diapers, so that the caregiver needs to clean and changes new diaper when it is contaminated. Resistance occurs at first because of the uncomfortable and indignity feels.

Accordingly, some manufactures have developed a machine or an equipment for excrement cleaning job to replace the diapers. However, the drawback of current cleaning machine (equipment) isn't simple to use as the diaper. The caregiver put the equipment on the people when he/she has needs, and then removes the equipment when it finishes the cleaning.

Therefore, a new equipment can clean excrement efficiently is necessary, it can make people happier and comfortable; it is the most important goal for current manufactures.

SOME EXEMPLARY EMBODIMENTS

According to those above mentioned drawbacks, these and other needs are addressed by the present disclosure, wherein an approach is provided for a device that integrates excrement collecting, cleaning and wearable functions which can make people without autonomy to clean up excrement by themselves easily.

According to one aspect of an embodiment of the present disclosure, a device for cleaning excrements comprises an outer cover, an inner body and a cleaning machine. The outer cover has at least one first connector and a first opening. The one first connector is mounted inside the outer cover. The first opening is formed at the bottom of the outer cover, and is corresponded to the anus of a person. The inner body is in a cup shape that protrudes and covers the person from the bladder along the groin toward the bottom vertebra of the buttock.

The inner body further comprises a second connector, a second opening, at least one sensor and a cleaning assembly. The second connector is configured for connecting the first connector. The second opening is corresponded to the first opening, and is formed at the bottom of the inner body and connects to a tube. The one sensor is mounted inside the inner body, is electrically connected to the cleaning machine, and is configured for sensing an excrement and triggering the cleaning machine to collect the excrement through the tube. The cleaning assembly is connected to the cleaning machine, and is configured for cleaning the person.

According to another aspect of an embodiment of the present disclosure, a method for cleaning excrements is able to provide clean and comfortable cleaning operation that comprises acts of flushing, suction, injection and drying.

There are two setting steps of flushing comprises which include an urinal mode or a feces mode based on the sensed result of the excrement that appears on underwear of the person, to set up the mode for a male mode or a female on the cleaning machine, flushing anus of the person with a rear nozzle and flushing a front portion of the underwear simultaneously when the cleaning machine is in the male mode, and flushing anus and urinary organs of the person with the rear nozzle when the cleaning machine is in the female mode.

Accordingly, the device and the method of the present invention are able to assist people without autonomy to clean up excrements alone, to clean excrement efficiently and makes them more comfortable.

DESCRIPTION OF THE PREFERRED EMBODIMENT

Figure 1:
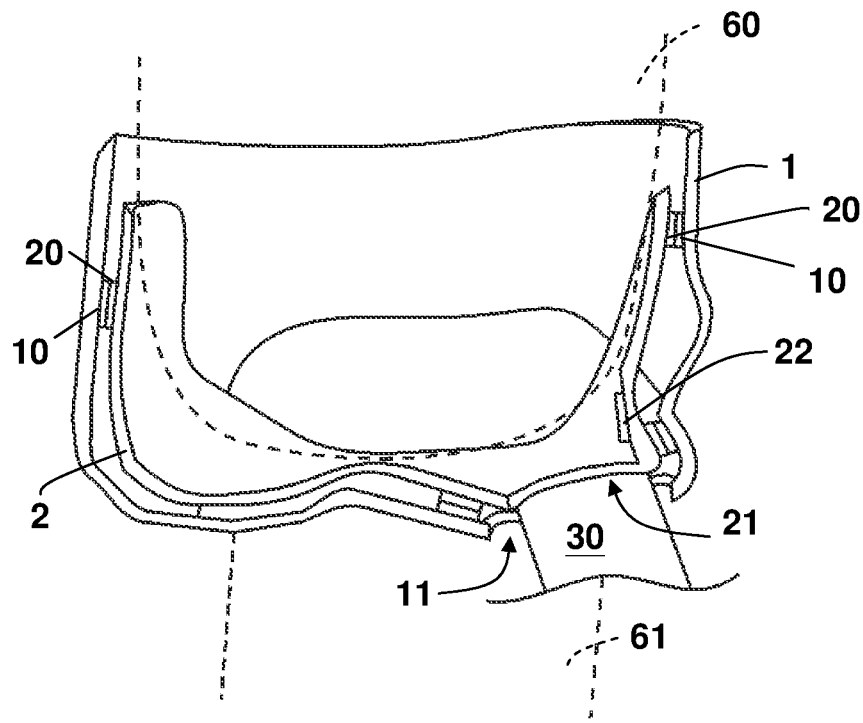
FIG. 1 is a diagram of illustrating a device being worn for in accordance with an embodiment of the present invention.
Figure 2:
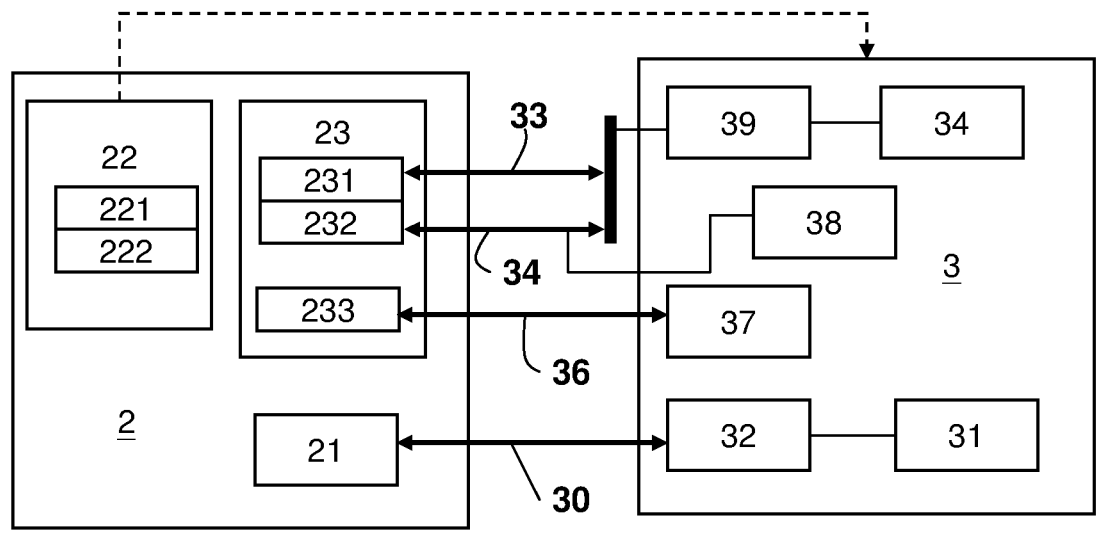
FIG. 2 is a structure diagram of the cleaning machine in accordance with an embodiment of the present disclosure.

With reference to FIGS. 1 and 2. FIG. 1 is a diagram of illustrating a device being worn for in accordance with an embodiment of the present invention, and FIG. 2 is a structure diagram of the cleaning machine.

In this embodiment, the device for cleaning excrements comprises an outer cover 1, an inner body 2 and a cleaning machine 3. As shown in FIG. 1, the outer cover 1 is a underwear that is wearable to a person's buttock 60. The outer cover 1 has at least one first connector 10 and a first opening 11. The first opening 11 is formed at the bottom of the outer cover 1 corresponded to an anus of a person. The inner body 2 in a cup shape that protrudes and covers the person from the bladder along the groin 61 toward the bottom vertebra of the buttock. The second connector 20 is configured for connecting the first connector, which forms the underwear. In an embodiment, the first connector 10 and the second connector 20 is but not limited to be a Velcro.

The inner body 2 has the second connector 20, a second opening 21, at least one sensor 22 and a cleaning assembly 23. The second opening 21 is corresponded to the first opening 10, and is formed at the bottom of the inner body 2 and connects to a tube 30. The one sensor 22 is mounted inside the inner body 2, is electrically connected to the cleaning machine 3, and is configured for sensing an excrement and triggering the cleaning machine 3 to collect the excrement through the tube 30. The cleaning assembly 23 is connected to the cleaning machine 3, and is configured for cleaning the person.

Figure 3:
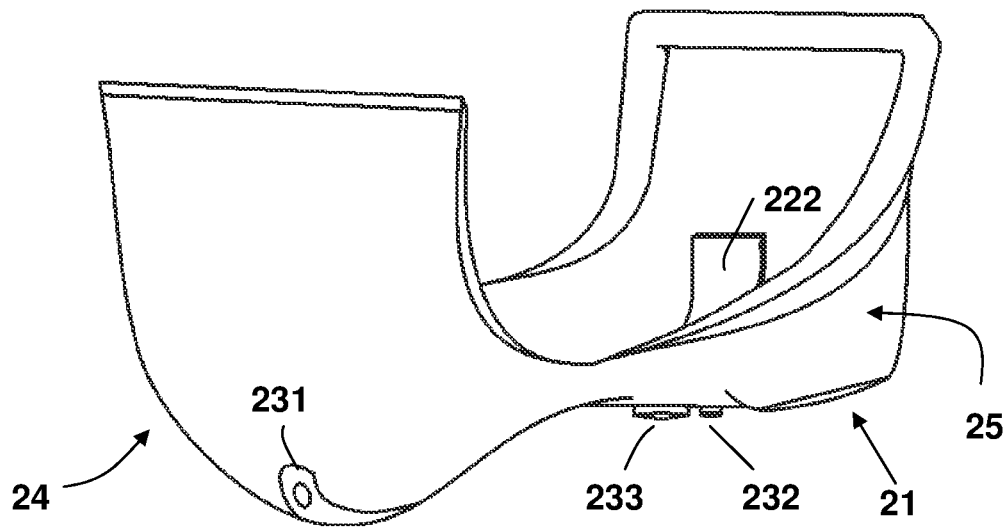
FIG. 3 is a side view diagram of the inner body in accordance with an embodiment of the present disclosure.
Figure 4:
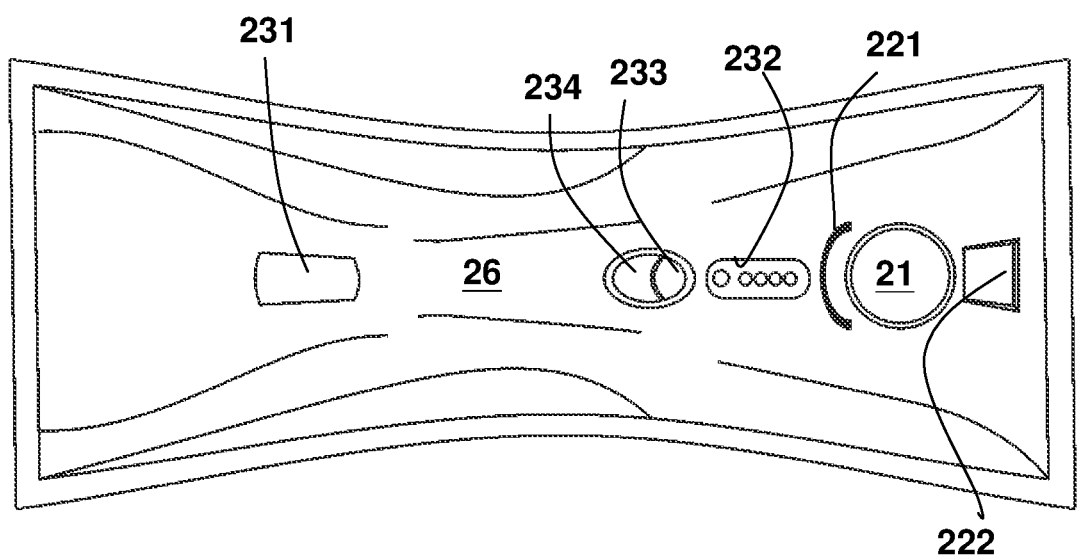
FIG. 4 is a top view diagram of FIG. 3.

With reference to FIGS. 3 and 4, the inner body 2 has a front portion 24, a rear portion 25 and a guiding channel 26. The front portion 24 covers the bladder of the person. The rear portion 25 covers the buttock of the person. The guiding channel 26 is formed between the front portion 24 and the second portion 25, and is configured for guiding the urine-like excrement from the front portion 24 toward the rear portion 25.

The one sensor 22, in an embodiment, includes a first sensor 221 and a second sensor 222. The first sensor 221 is located adjacent to the second opening 21. Excrements such as urine flows to the second opening 21 can be detected so that the first sensor 221 is able to inform the cleaning machine 3. The second sensor 222 is located at the rear portion 25 of the inner body 2. Excrements such as feces can be detected within the sensing range of the second sensor 222. The second sensor 222 informs the cleaning machine 3 when excrements have been detected.

As shown in FIG. 2, the cleaning machine 3 further comprises a suction motor 31 and collecting bucket 32. The first sensor 221 or the second sensor 222 will drive cleaning machine 3 triggers the suction motor 31 to collect the excrement to the collecting bucket 32 via the tube 30 when the excrement is sensed.

With reference to FIGS. 3 and 4, FIG. 3 is a side view diagram of the inner body in accordance with an embodiment of the present disclosure, and FIG. 4 is a top view diagram of FIG. 3. The cleaning assembly 23 comprises a front nozzle 231, a rear nozzle 232 and a hot wind outlet 233. The front nozzle 231 is coupled to the front portion 24 of the inner body 2 adjacent to the guiding channel 26, and is connected to a water tank 34 of the cleaning machine 3 through a first pipe 33. The first pipe 33 leads the water of the water tank 34 by a water pump 39 to the front nozzle 231. The front nozzle 231 flushes the inner surface of the inner body 2 from the front portion 24 to the rear portion 25.

With reference to FIGS. 2 and 4, the cleaning assembly 23, include the rear nozzle 232, the hot wind outlet 233, the rear nozzle 232 is coupled to the rear portion 25 of the inner body 2, and is connected to the water tank 24 of the cleaning machine 3 through the second pipe 35. The second pipe 35 leads the water of the water tank 34 by a water pump 39 to the rear nozzle 232. The rear nozzle 232 flushes the anus and/or urinary organs of the person.

In order to enhance cleaning, the cleaning machine 3 further comprises an air pump 38. The air pump 38 is connected to the rear nozzle 232 through the second pipe 35. When excrements have been collected to the collecting bucket 32, and the organs and/or anus are flushed, the air pump 38 injects outside air into the inner body 2 to the organs and/or anus that removes sewage.

The hot wind outlet 233 is formed on the guiding channel 26, and is connected to a hot wind blower 37 of the cleaning machine 3 through air pipe 36. The hot wind blower 37 generates hot air that is leaded by the air pipe 36 into the inner body 2 for drying.

It is noted that since the hot wind outlet 233 is mounted on the guiding channel 26, to avoid urine-like excrement or fluid may flow into the hot wind outlet 233. The hot wind outlet 233 is protruded inwardly toward the inside of the inner body 2. The protrusion of the hot wind outlet forms a shelter 234. For a person in bed position, urine-like excrement flow through the guiding channel 26 will shelter and directly fall to the rear portion 25.

Figure 5:
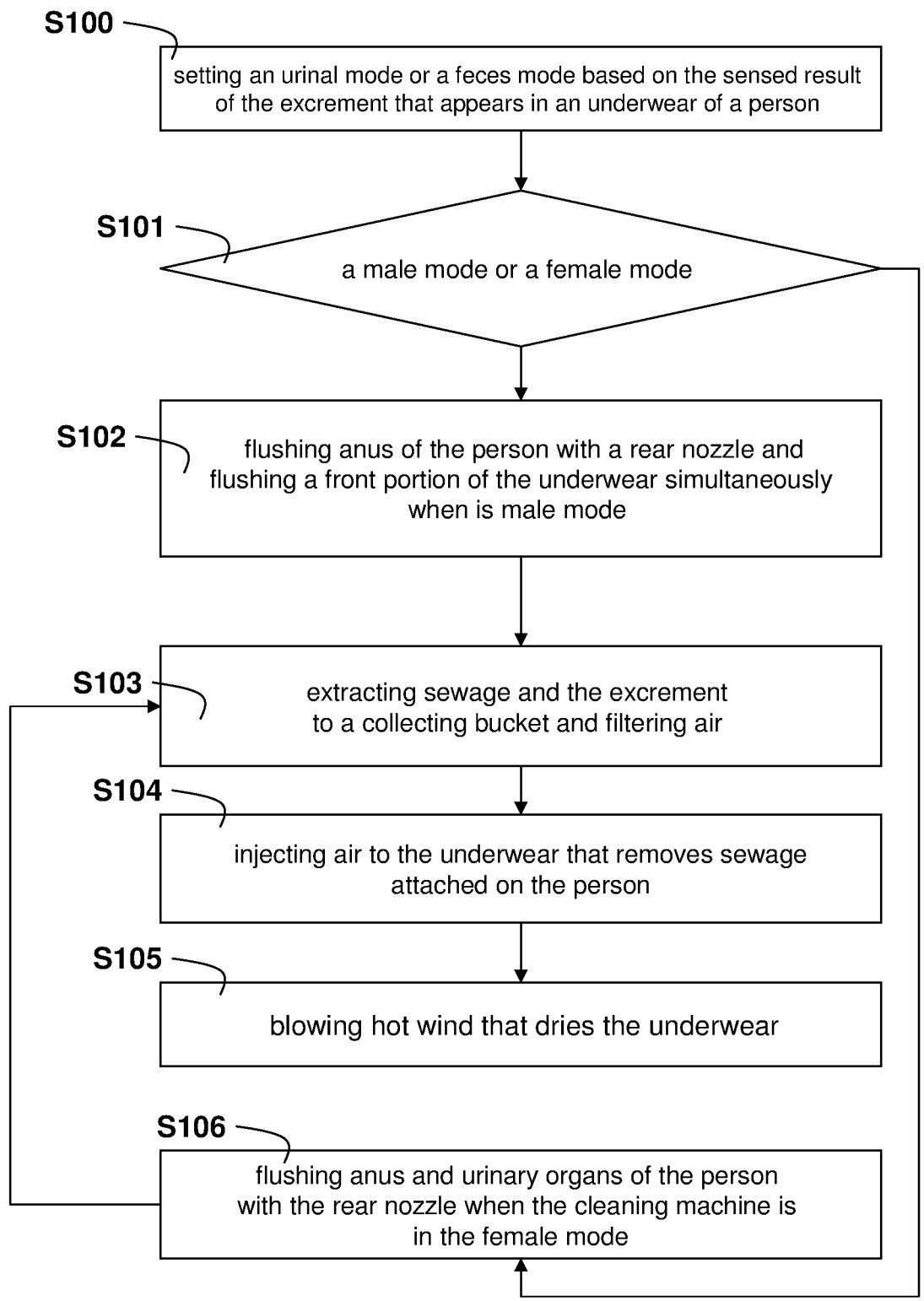
FIG. 5 is a flow diagram illustrating a method for cleaning excrements in accordance with an embodiment of the present disclosure.

With reference to FIG. 5, FIG. 5 is a flow diagram illustrating a method for cleaning excrements in accordance with an embodiment of the present disclosure. In one embodiment, the method for cleaning excrements is able to dynamically change the cleaning process based on different sexual and different type of excrements (e.g., urine or feces). The method applying to a sensor to senses excrements inside a underwear of a person, which comprises acts of:

S100 setting an urinal mode or a feces mode based on the sensed result of the excrement that appears in an underwear of a person;

S101 setting a male mode or a female mode to the cleaning machine;

S102 the cleaning machine flushing anus of the person with a rear nozzle and flushing a front portion of the underwear simultaneously when is male mode;

S103 extracting sewage and the excrement to a collecting bucket and filtering air;

S104 injecting air to the underwear that removes sewage attached on the person; and S105 blowing hot wind that dries the underwear.

The underwear is waterproof.

With reference to FIG. 5, in S106: The method further comprises an act of flushing anus and urinary organs of the person with the rear nozzle when the cleaning machine is in the female mode. The male mode and female mode can be preset before the excrement being sensed. However, a female user can also use male mode for cleaning. Due to male's urinary organs structure, which does not need addition wash after discharge. Hushing the inner wall the flow with urine to remove odor and keep the underwear clean are enough.

Figure 6:
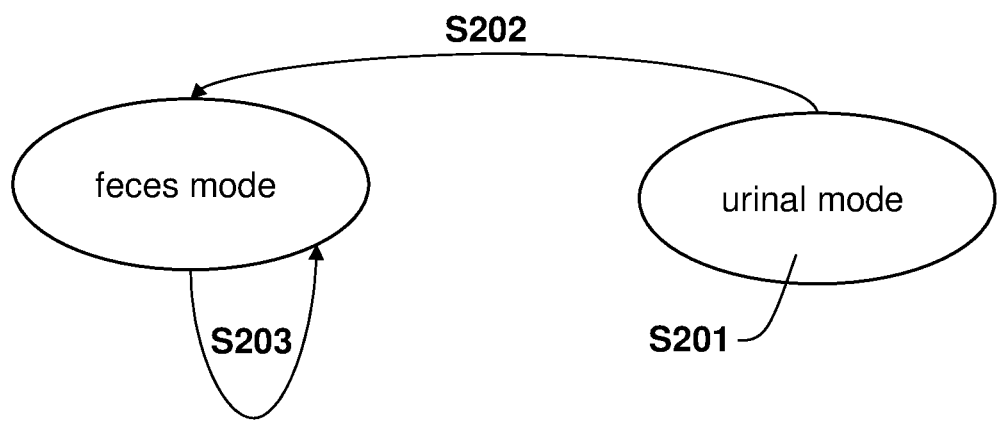
FIG. 6 is a diagram of showing mode switches of the method in accordance with an embodiment of the present disclosure.

With reference to FIG. 6, FIG. 6 a diagram of showing mode switches of the method in accordance with an embodiment of the present disclosure. In present invention, the feces mode and urinal mode are basically determined by two sensors (i.e., the first sensor and the second sensor) to sense the type of the excrements. The cleaning machine then provides different cleaning time, water for cleaning. The method further comprises a switch rule that comprises acts of:

S201 setting the cleaning machine in the urinal mode when the first sensor sensed the excrement;

S202 in urinal mode, switching to feces mode when the second sensor sensed the excrement; and S203 in feces mode, locking the mode switch when the first sensor sensed the excrement.

Accordingly, based on above mentioned switch rule, the machine and cleaning method can be ensured that use correct way to clean the person, and makes sure that it will not use urinal mode to deal with feces discharge.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A device for cleaning excrements for people without autonomy, the device comprising:
   a cleaning machine;
   an outer cover having:
      at least one first connector being mounted inside the outer cover; and
      a first opening formed at the bottom of the outer cover corresponding to an anus of a person; and
   an inner body being in a cup shape that protrudes and covers the person from the bladder along the groin toward the bottom vertebra of the buttock, and the inner body having:
      a second connector being configured for connecting the first connector;

a second opening being corresponded to the first opening, and being formed at the bottom of the inner body and connects to a tube;
a front portion covering the bladder of the person;
a rear portion covering the buttock of the person; and
a guiding channel formed between the front portion and the rear portion;

at least one sensor being mounted inside the inner body, being electrically connected to the cleaning machine, and being configured for sensing an excrement and triggering the cleaning machine to collect the excrement through the tube; and a cleaning assembly being connected to the cleaning machine, and being configured for cleaning, and comprising:
a front nozzle coupling to the front portion of the inner body adjacent to the guiding channel, and connecting to a water tank of the cleaning machine through a first pipe;
a rear nozzle coupling to the rear portion of the inner body, and connecting to the water tank of the cleaning machine through the second pipe; and
a hot wind outlet formed on the guiding channel, connecting to a hot wind blower of the cleaning machine through an air pipe and having a shelter.

2. The device as claimed in claim 1, wherein the one sensor comprises:
a first sensor located adjacent to the second opening; and
a second sensor located at a rear portion of the inner body.

3. The device as claimed in claim 2, wherein the cleaning machine has a suction motor and collecting bucket, the first sensor or the second sensor triggers the suction motor to collect the excrement to the collecting bucket via the tube when the excrement is sensed.

4. The device as claimed in claim 1, wherein the sensor comprises:
a first sensor located adjacent to the second opening; and
a second sensor located at the rear portion of the inner body.

5. The device as claimed in claim 1, wherein the cleaning machine further comprises an air pump, and the air pump is connected to the rear nozzle through the second pipe.

6. A method for cleaning excrements when a cleaning machine senses an excrement, the method comprising acts of:
setting an urinal mode or a feces mode based on the sensed result of the excrement that appears in an underwear of a person;
setting a male mode or a female mode to the cleaning machine;
the cleaning machine flushing anus of the person with a rear nozzle and flushing a front portion of the underwear simultaneously when is male mode;
extracting sewage and the excrement to a collecting bucket and filtering air;
injecting air to the underwear that removes sewage attached on the person; and
blowing hot wind that dries the underwear.

7. The method as claimed in claim 6, further comprising an act of flushing anus and urinary organs of the person with the rear nozzle when the cleaning machine is in the female mode.

8. The method as claimed in claim 6, wherein the male mode and female mode is preset before the excrement is sensed.

9. The method as claimed in claim 6, further comprising a switch rule using a first sensor and a second sensor, wherein the switch rule comprises:
setting the cleaning machine in the urinal mode when the first sensor sensed the excrement;
in urinal mode, switching to feces mode when the second sensor sensed the excrement; and
in feces mode, locking the mode switch when the first sensor sensed the excrement.

* * * * *